(12) United States Patent
Rizzo et al.

(10) Patent No.: US 8,563,718 B2
(45) Date of Patent: Oct. 22, 2013

(54) THIAZOLYL-PYRAZOLOPYRIMIDINE COMPOUNDS AS SYNTHETIC INTERMEDIATES AND RELATED SYNTHETIC PROCESSES

(75) Inventors: John Robert Rizzo, Brownsburg, IN (US); Sathish Kumar Boini, West Lafayette, IN (US); Radhe Krishan Vaid, Westfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 121 days.

(21) Appl. No.: 13/063,226

(22) PCT Filed: Sep. 29, 2009

(86) PCT No.: PCT/US2009/058722
§ 371 (c)(1), (2), (4) Date: Mar. 10, 2011

(87) PCT Pub. No.: WO2010/039678
PCT Pub. Date: Apr. 8, 2010

(65) Prior Publication Data
US 2011/0166345 A1    Jul. 7, 2011

Related U.S. Application Data

(60) Provisional application No. 61/102,153, filed on Oct. 2, 2008.

(51) Int. Cl.
*C07D 487/00* (2006.01)

(52) U.S. Cl.
USPC ........................................................ 544/281

(58) Field of Classification Search
None
See application file for complete search history.

(56) References Cited

U.S. PATENT DOCUMENTS

| 8,030,304 B2 * | 10/2011 | Chen et al. ................. 514/247 |
| 2009/0076266 A1 | 3/2009 | Daugulis et al. |

FOREIGN PATENT DOCUMENTS

| WO | 2008/036579 A1 | 3/2008 | |
| WO | WO2008/036579 | * 3/2008 | ........... C07D 487/04 |

OTHER PUBLICATIONS

Do, Hien-Quang et. al; Copper-catalyzed arylation of C-H bonds; Abstracts of Papers, 236th ACS National Meeting, New Orleans, LA, Apr. 6-10, 2008, Accession No. 2008:390596.
Vattoly J. Majo et al.; Facile Palladium-Catalyzed Synthesis of 3-Arylpyrazolo-[1,5-a]pyrimidines, Adv. Synth. Catal. 2003, 345, 620-624.
Hein-Quang D. et al; A General Method for Copper-Catalyzed Arylation of Arene C-H Bonds, JACS, 2008, 130, 15185-15192.
Hien-Quang Do. et al; Copper-Catalyzed Arylation and Alkenylation of Polyfluoroarene C-H Bonds, JACS, 2008, 130, 1128-1129.
Hien-Quang Do et al.; Copper-Catalyzed Arylation of Heterocycle C-H Bonds, JACS, 2007, 129, 12404-12405.

* cited by examiner

*Primary Examiner* — Jeffrey Murray
(74) *Attorney, Agent, or Firm* — R. Craig Tucker

(57) ABSTRACT

The present invention relates to a synthetic intermediate of the formula:

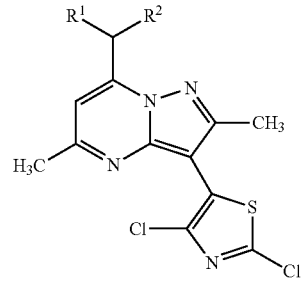

and its use in a synthetic process to make compounds of the formula

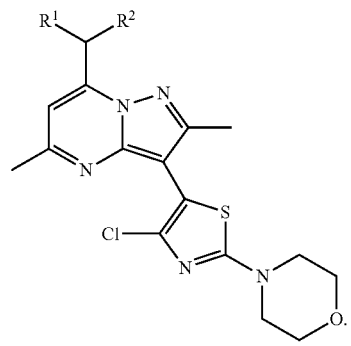

18 Claims, No Drawings

THIAZOLYL-PYRAZOLOPYRIMIDINE COMPOUNDS AS SYNTHETIC INTERMEDIATES AND RELATED SYNTHETIC PROCESSES

This invention relates to novel intermediates and processes in the synthesis of thiazolyl-pyrazolopyrimidine compounds, which final compounds are useful as CRF-1 receptor antagonists for the treatment of certain psychiatric and neuroendocrine disorders.

Corticotropin releasing factor (CRF) is a peptide hypothalamic hormone which also has a broad spectrum of physiological effects consistent with a neurotransmitter or neuromodulator role in the brain. CRF has been implicated in a wide range of psychiatric disorders and neurological diseases including alcohol and substance abuse and associated withdrawal symptoms, as well as depression and anxiety. CRF-1 receptor antagonists have particularly been implicated for the treatment of alcohol dependency and depression.

Certain thiazolyl-pyrazolo[1,5-a]pyrimidines have been found to be particularly useful as CRF-1 antagonists, as for example 7-(1-ethyl-propyl)-3-(4-chloro-2-morpholin-4-yl-thiazol-5-yl)-2,5-dimethyl-pyrazolo[1,5-a]pyrimidine and 7-(1-propyl-butyl)-3-(4-chloro-2-morpholin-4-yl-thiazol-5-yl)-2,5-dimethyl-pyrazolo[1,5-a]pyrimidine, as described in WO 2008/036579. Recent advances in copper catalyzed arylation reactions with different substrates have been described in J. Am. Chem. Soc., vol. 130, pg. 1128-1129 (2008).

The present invention provides novel synthetic intermediates and synthetic processes using said intermediates to make thiazolyl-pyrazolo[1,5-a]pyrimidine CRF-1 receptor antagonists more economically and in higher yields. Certain embodiments of the presently claimed processes also avoid the use of mutagenic materials and environmentally toxic catalysts, as compared to previously known synthetic methods, as for example, those disclosed in WO 2008/036579.

In one aspect of the present invention, there is provided a compound of Formula I

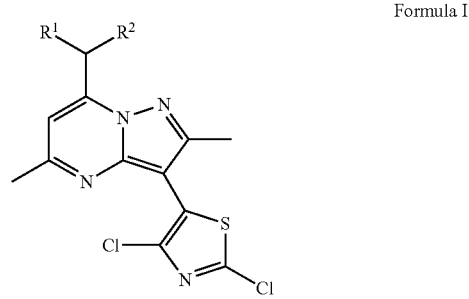

Formula I wherein:

$R^1$ and $R^2$ are independently ethyl or n-propyl.

In one preferred embodiment, $R^1$ and $R^2$ are each ethyl. In a second preferred embodiment, $R^1$ and $R^2$ are each n-propyl.

In another aspect of the present invention, there is provided a synthetic process for preparing a compound of the Formula II

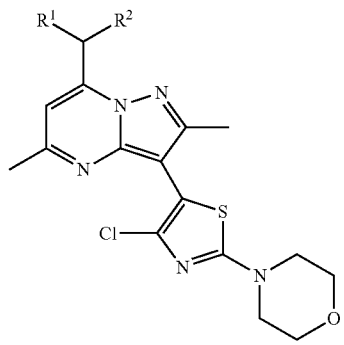

II wherein $R^1$ and $R^2$ are independently ethyl or n-propyl, comprising the steps of i) reacting a compound of Formula III,

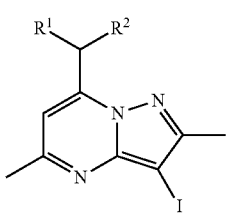

III or a salt thereof, with 2,4-di-chlorothiazole, or a salt thereof, in the presence of a copper halide catalyst, a ligand selected from 1,10-phenanthroline and bipyridine, and a base selected from $K_3PO_4$ and $Cs_2CO_3$, to form a compound of Formula I (above); and ii) reacting the compound of Formula I, with morpholine, or a salt thereof, in the presence of a suitable inorganic base.

In one preferred embodiment of this aspect of the invention, $R^1$ and $R^2$ are each ethyl. In a second preferred embodiment of this aspect of the invention, $R^1$ and $R^2$ are each n-propyl.

Suitable copper halide catalysts include CuI, CuBr, and CuCl. CuCl is preferred.

Use of a copper ligand facilitates the efficient catalysis by the copper ion. Both 1,10-phenanthroline and bipyridine are effective ligands in the present process. 1,10-phenanthroline is preferred. When bipyridine is used, higher mole percents of bipyridine and copper are needed for high yields, as for example from about 0.9 to about 1.1 equivalents, say about 1 equivalent bipyridine, and from about 0.5 to about 1.1 equivalents of the copper source, say about 1 equivalent of the copper source, with CuCl being preferred.

When 1,10-phenanthroline is used, it may be effectively used in catalytic amounts, and with catalytic amounts of the copper source, as for example from about 5-50 mole percent each (0.05-0.50 equivalents), with CuCl being the preferred copper source. In one embodiment, the 1,10-phenanthroline and the copper catalyst, say CuCl, are used at about 5-50 mole percent (0.05-0.50 equivalents). In another embodiment, the 1,10-phenanthroline and the copper catalyst, say CuCl, are used at about 10±1 mole percent (0.10 equivalents). In yet another embodiment, the 1,10-phenanthroline and the copper catalyst, say CuCl, are used at about 30±1 mole percent (0.30 equivalents).

The reaction of step i) is base driven and is sensitive to the base selected. The dichlorothiazole reagent is base and temperature labile and is susceptible to degradation if the selected base is too strong and/or the reaction temperature is too high, as for example with t-butoxy lithium or t-butoxy potassium and/or at temperatures higher than about 120° C. As such, suitable bases for step i) are $K_3PO_4$ and $Cs_2CO_3$, with $Cs_2CO_3$— being preferred. Likewise, it is preferred that the reaction of step i) be run at a temperature of from about 80 to 120° C.

The reaction of step i) is less sensitive to the solvent selected with suitable solvents being aprotic solvents, as for example 1,4-dioxane, 2-MeTHF, DMAC, CPME, propanenitrile, 2-MeTHF/DMAC, n-BuOAc and DMF. The co-solvent system of 2-MeTHF/DMAC with proportions in the range of 70/30 to 80/20 being preferred, as for example 80/20 2-MeTHF/DMAC.

The reaction of step ii) is less sensitive to the inorganic base and solvent selected. Suitable bases include $K_2CO_3$, $Cs_2CO_3$, $Na_2CO_3$, $K_3PO_4$, NaOH, and the like. $K_2CO_3$ and $K_3PO_4$ are preferred with $K_2CO_3$ being particularly preferred.

Suitable solvents for the reaction of step ii) include most polar solvents, such as methanol, ethanol, n-propanol, 2-propanol, n-butanol, acetonitrile, 2-MeTHF, and morpholine. Morpholine is preferred in that it is an excellent solvent and a reactant in the reaction of step ii).

Preferred reaction temperatures for the reaction of step ii) are from about 60-120° C.

In one preferred embodiment of the present invention, the synthetic process comprises the steps of:

i) reacting a compound of Formula III,

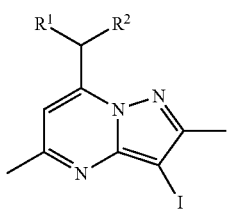

III or a salt thereof, wherein $R^1$ and $R^2$ are independently ethyl or n-propyl, with 2,4-di-chlorothiazole, or a salt thereof, in the presence of CuCl, 1,10-phenanthroline, and a base selected from $K_3PO_4$ and $Cs_2CO_3$, to form a compound of Formula I (above); and ii) reacting the compound of Formula I, with morpholine, or a salt thereof, in the presence of $K_2CO_3$.

It is further preferred in this embodiment of the process that the reaction of step i) use from about 5-50 mole percent, particularly about 30 mole percent, CuCl and from about 5-50 mole percent, particularly about 30 mole percent, 1,10-phenanthroline with 2-MeTHF/DMAC (particularly about 80/20 2-MeTHF/DMAC) as a solvent system and that the reaction be run at from about 80 to 120° C., and that the reaction of step ii) use morpholine as a solvent and $K_2CO_3$ as the base.

In a another aspect of the invention, there is provided a synthetic process for preparing a compound of the formula

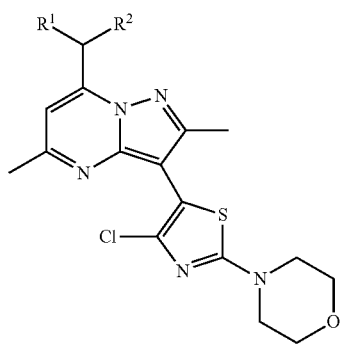

wherein $R^1$ and $R^2$ are independently ethyl or n-propyl, comprising the steps of
i) reacting a compound of the formula

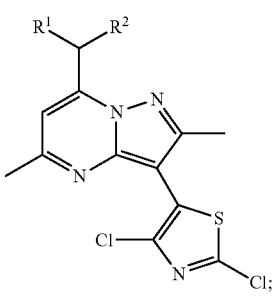

or a salt thereof, with an excess of morpholine or salt thereof, in the presence of a suitable solvent.

One embodiment of this aspect of the invention provides a synthetic process for preparing a compound of the formula

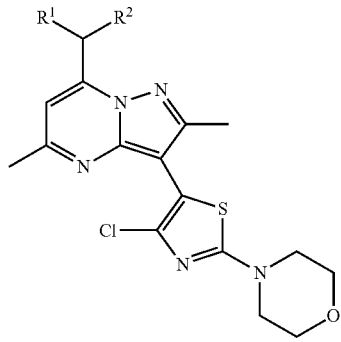

wherein $R^1$ and $R^2$ are independently ethyl or n-propyl, comprising the steps of
i) reacting a compound of the formula

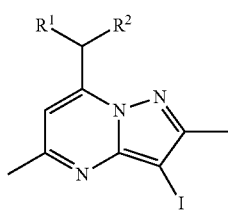

or a salt thereof, with 2,4-di-chlorothiazole, or a salt thereof, in the presence of a copper halide catalyst, a ligand selected from 1,10-phenanthroline and bipyridine, and a base selected from $K_3PO_4$ and $Cs_2CO_3$, to form a compound of the formula

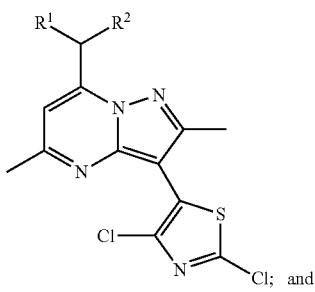
Cl; and ii) reacting the product of step i), with an excess of morpholine, or a salt thereof, in a suitable solvent.

In this aspect of the invention, various aprotic solvents may be suitable, but preferred solvents are 2-MeTHF and 2-propanol. In a preferred embodiment, 2-propanol is used as solvent. It is surprisingly found that use of 2-propanol reduces reaction times about three fold over prior solvent systems tested. It is also surprisingly found that use of 2-propanol provides the desired amination product in high purity even in the presence of competing nucleophilic alcohol. Use of 2-propanol also further simplifies the work up of the final product by allowing crystallization directly from this solvent, thus avoiding a further solvent exchange prior to crystallization.

In this aspect of the invention, it has also been surprisingly found that morpholine can function as a suitable base for the amination reaction, thus eliminating the need for an additional base to drive the reaction. Additionally, yields are improved while maintaining quality of final product. Reduction of the amount of morpholine used is also of benefit in the final workup of the product. In one embodiment wherein 2-MeTHF is used as the solvent, the reaction is run with between about 4.0 and about 6.0 equivalents, say about 5.35 equivalents, of morpholine, or salt thereof. In another embodiment wherein 2-propanol is used as the solvent, the reaction is run with between about 3.0 and about 4.0 equivalents, say about 3.3 equivalents, of morpholine, or salt thereof.

Thus in one embodiment of the invention, there is provided a synthetic process for preparing a compound of the formula

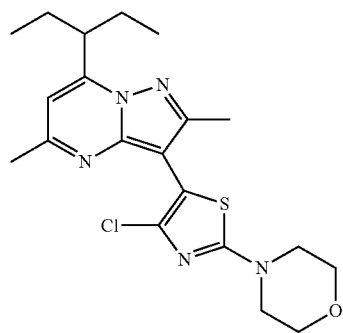 [SMILES: CCC(CC)c1cc(C)nc2c(-c3sc(N4CCOCC4)nc3Cl)c(C)nn12]

comprising the steps of
i) reacting a compound of the formula

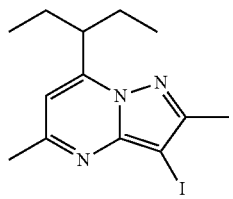

or a salt thereof, with 2,4-di-chlorothiazole, or a salt thereof, in the presence of copper chloride, 1,10-phenanthroline, and $Cs_2CO_3$, to form a compound of the formula

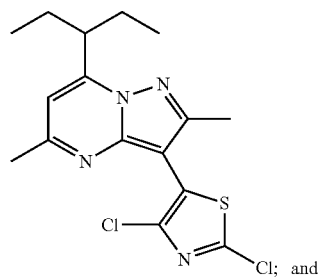 [SMILES: CCC(CC)c1cc(C)nc2c(-c3sc(Cl)nc3Cl)c(C)nn12 ; "and"]
Cl; and ii) reacting the product of step i), with an excess of morpholine, or a salt thereof, in 2-propanol as a solvent.

Abbreviations use in this application are as follows:
CPME means cyclopentyl methyl ether.
DMAC means N,N-dimethylacetamide.
DMF means dimethylformamide.
EtOAc means ethylacetate.
2-MeTHF means 2-methyltetrahydrofuran.
2-MeTHF/DMAC system means 2-methyltetrahydrofuran and N,N-dimethylacetamide in a co-solvent system in proportions between about 70/30 and about 80/20.
n-BuOAc means n-butylacetate.
XRPD means X-ray powder diffraction.
DSC means differential scanning calorimetry.

Further preferred embodiments for the synthetic process of the present invention are as described in the examples below.

EXAMPLES

Example 1

7-(1-ethyl-propyl)-3-(2,4-dichloro-thiazol-5-yl)-2,5-dimethyl-pyrazolo[1,5-a]pyrimidine

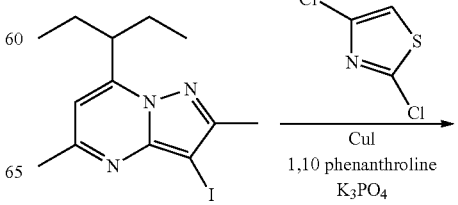

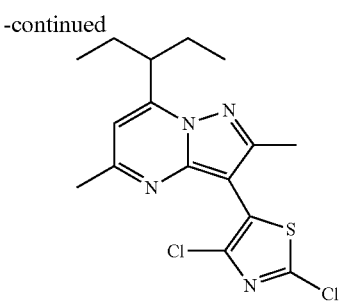

Charge 7-(1-ethyl-propyl)-3-iodo-2,5-dimethyl-pyrazolo [1,5-a]pyrimidine (1.03 g, 3.00 mmoles), K$_3$PO$_4$ (1.95 g, 9.00 mmoles), 2,4-dichlorothiazole (0.58 g, 3.75 mmoles), 1,10 phenanthroline (0.05 g, 0.30 mmoles) and anhydrous DMAC (5 mL) to a round bottom flask equipped with a magnetic stir bar, thermal couple and N$_2$ inlet. Degas the yellow heterogeneous reaction mixture with N$_2$ (gas) for 30 min. and then add CuI (0.06 g, 0.30 mmoles) in one portion followed by additional 30 min. degassing with N$_2$ (gas). Stir the reaction mixture at 120° C. for about 6 hr. Cool the reaction mixture to room temperature overnight, add toluene (10 mL) and stir for 1 hr. Purify the mixture through silica gel eluting with toluene (10 ml). Extract with 1 M HCl (10 mL), water (10 mL), brine (10 mL) and concentrate under reduced pressure to give a yellow solid. Recrystallize the solid from methanol (5 ml) to yield the title compound as a yellow crystalline solid. (0.78 g, 70% yield, >99% pure by LC) MS (ES)=369 (M+1). $^1$H NMR (CDCl$_3$)=6.5 (1H, s); 3.6 (1H, m); 2.6 (3H, s); 2.5 (3H, s); 1.9 (4H, m); 0.9 (6H, t).

Example 2

7-(1-ethyl-propyl)-3-(4-chloro-2-morpholin-4-yl-thiazol-5-yl)-2,5-dimethyl-pyrazolo[1,5-a]pyrimidine

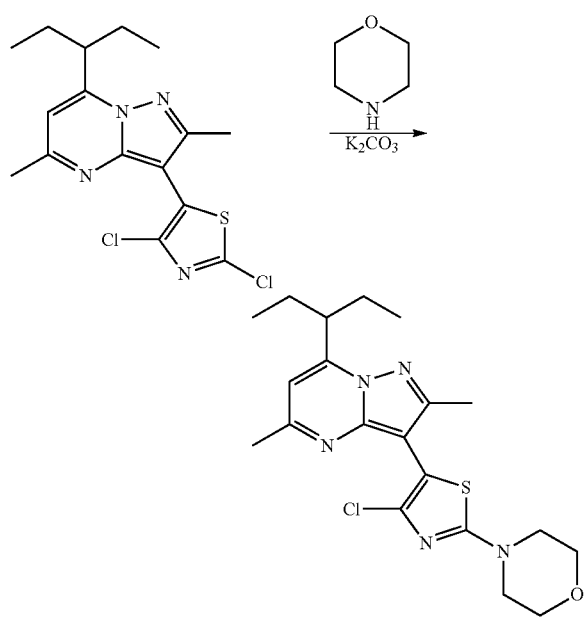

Charge 7-(1-ethyl-propyl)-3-(2,4-dichloro-thiazol-5-yl)-2,5-dimethyl-pyrazolo[1,5-a]pyrimidine (0.37 g, 1.00 mmoles), K$_2$CO$_3$ (0.28 g, 2.00 mmoles) and anhydrous morpholine (3 mL) to a round bottom flask equipped with a magnetic stir bar and N$_2$ inlet. Stir the yellow mixture at 100° C. for about 4 hr., during which time the reaction becomes homogeneous. Cool the reaction mixture to room temperature, add H$_2$O (10 mL) and stir the heterogeneous reaction mixture overnight at room temperature. Collected the yellow solid by filtration, wash with H$_2$O and allowed to air dry overnight to give the crude title compound (391 mg). Recrystallize from isopropyl alcohol (3 mL) to yield the title compound as a light yellow crystalline solid (380 mg, 90.6% yield, >99% by LC). MS (ES)=420 (M+1). $^1$H NMR (CDCl$_3$)= 6.45 (1H, s); 3.81 (m, 4H); 3.62 (1H, m); 3.50 (m, 4H); 2.6 (3H, s); 2.45 (3H, s); 1.85 (4H, m); 0.9 (6H, t).

Example 3

The reactions of Example 1 are run with various other catalysts, ligands, bases and solvents, which are found to have the following effects on yield of 7-(1-ethyl-propyl)-3-(2,4-dichloro-thiazol-5-yl)-2,5-dimethyl-pyrazolo[1,5-a]pyrimidine. (See Tables 1-4).

TABLE 1

Evaluation of different ligands

| Ligand | % Product |
|---|---|
| 2,2'-bipyridine | 72.7 |
| 1,10-phenanthroline | 84.7 |
| L-proline | 23.7 |
| 2-acetylcyclohexanone | 19.0 |

(Reactions are carried out in parallel reactors with 1.2 mmol 2,4-dichlorothiazole, 1 mmol 7-(1-ethyl-propyl)-3-iodo-2,5-dimethyl-pyrazolo[1,5-a]pyrimidine, 0.5 mmol CuI, 0.5 mmol ligand and 2.1 mmol Cs$_2$CO$_3$ in 4 mL DMAC. The reactions are degassed under N$_2$ for 30 min. and then heated at between 80 and 100° C. overnight under N$_2$. Percent product is measured as the percent of total area under the HPLC curve for the product peak. Longer reaction times are shown in parenthesis)

TABLE 2

Evaluation of various solvents

| Solvent | % Product |
|---|---|
| DMAC | 82.4 |
| 10% H$_2$O in DMAC | 1.6 |
| DMAC (under air) | 8.5 |
| DMF | 76.9 |
| 1-methyl-2-pyrrolidinone (NMP) | 77.3 |
| Dioxane | 69.5 |
| THF | 66.9 |
| Toluene | 23.0 |
| Ethylene glycol dimethyl ether (DME) | 60.8 |
| Dimethyl sulfoxide (DMSO) | 76.7 |
| Propanenitrile [CuCl catalyst] | 99 |
| Acetonitrile [CuCl catalyst] | 8 |
| 2-MeTHF [48 hr, CuCl catalyst] | 98 |
| BuOAc [24 hr, CuCl catalyst] | 98 |
| CPME [127 hr, with CuCl catalyst] | 87 |
| 2-MeTHF/DMAC (4:1) [14-24 hr, CuCl catalyst] | 98-100 |

(Reactions are carried out in parallel reactors with 1.2 mmol 2,4-dichlorothiazole 1 mmol 7-(1-ethyl-propyl)-3-iodo-2,5-dimethyl-pyrazolo[1,5-a]pyrimidine, 0.25 mmol CuI, 0.25 mmol 1,10-phenanthroline and 2.1 mmol Cs$_2$CO$_3$ in 3 mL specified solvent. The reactions are degassed under $N_2$ for 30 minutes and then heated at 100° C. overnight under $N_2$. Percent product is measured as the percent of total area under the HPLC curve for the product peak.)

TABLE 3

Evaluation of different copper sources

| Copper Source | % Product |
|---|---|
| CuCl | 81.3 |
| CuBr | 78.2 |
| CuI | 78.8 |

(Reactions are carried out in in parallel reactors with 1 mmol 2,4-dichlorothiazole 1 mmol 7-(1-ethyl-propyl)-3-iodo-2,5-dimethyl-pyrazolo[1,5-a]pyrimidine, 0.05 mmol CuX, 0.01 mmol 1,10-phenanthroline and 3 equivalents $K_3PO_4$ in 3 mL DMAC. The reactions are degassed under $N_2$ for 30 minutes and then heated at 100° C. overnight under $N_2$. Percent product is measured as the percent of total area under the HPLC curve for the product peak.)

TABLE 4

Evaluation of various inorganic bases

| Base | % Product |
|---|---|
| $Cs_2CO_3$ | 87.0 |
| $Cs_2CO_3$ (1.1 eq.) | 71.0 |
| $K_2CO_3$ | 25.6 |
| $Na_2CO_3$ | 6.0 |
| $Li_2CO_3$ | 1.8 |
| KOAc | 5.3 |
| $K_3PO_4$ | 83.8 |

(Reactions are carried out in in parallel reactors with 1 mmol 2,4-dichlorothiazole 1 mmol 7-(1-ethyl-propyl)-3-iodo-2,5-dimethyl-pyrazolo[1,5-a]pyrimidine, 0.1 mmol CuI, 0.1 mmol 1,10-phenanthroline and 2.1 mmol base and degassed for 30 minutes prior to the addition of 3 mL DMAC. The reactions are degassed under $N_2$ for 10 minutes and then heated at 100° C. overnight under $N_2$. Percent product is measured as the percent of total area under the HPLC curve for the product peak.)

Example 4

Use of Morpholine Both as a Reactant and Base in 2-MeTHF as Solvent

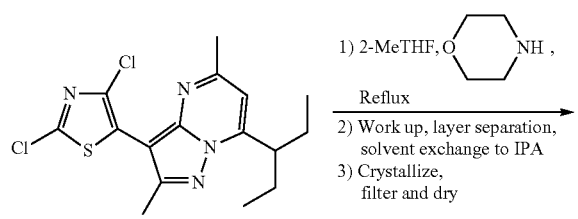

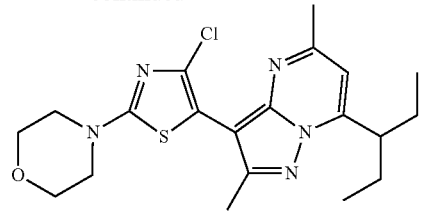

7-(1-ethyl-propyl)-3-(2,4-dichloro-thiazol-5-yl)-2,5-dimethyl-pyrazolo[1,5-a]pyrimidine (15.2 g, 41.16 mmoles) is charged into a 250 mL 3-necked round bottomed flask, followed by addition of 2-MeTHF (61 mL, 4.0 volumes), the yellowish brown slurry is stirred at about 20° C. for 5 min. Then morpholine (19 g, 218.18 mmoles) is added over 2-5 minutes. Contents are heated to reflux and maintained at reflux for 12 hr. The slurry is cooled to 25° C., followed by addition of 2-MeTHF (53 mL, 3.5 volumes) and water (38 mL 2.5 volumes). The reaction mixture is warmed to 40° C., where upon a homogenous solution with two distinct layers formed. The layers are separated, the organic layer is filtered and concentrated to ~3 volumes at atmospheric pressure. Four volumes 2-propanol (61 mL) are added. The solution is concentrated to ~3 volumes followed by addition of 4 volumes 2-propanol (61 mL), re-concentrated to ~3 volumes, followed by addition of another 6 volumes 2-propanol (91 mL), and refluxed for 15 min. The clear solution is gradually cooled to 75° C., seeded with 0.45 g 7-(1-ethyl-propyl)-3-(4-chloro-2-morpholin-4-yl-thiazol-5-yl)-2,5-dimethyl-pyrazolo[1,5-a]pyrimidine slurried in 2 mL 2-propanol, rinsed with an additional 2 mL 2-propanol and transferred to a crystallization flask. The slurry is cooled to between 0-5° C., maintained for 1 hr, filtered and the product rinsed with 2-propanol (30 mL, 2 volumes). The solid is dried at 60° C. in a vacuum oven to afford 16.92 g 7-(1-ethyl-propyl)-3-(4-chloro-2-morpholin-4-yl-thiazol-5-yl)-2,5-dimethyl-pyrazolo[1,5-a]pyrimidine. Purity of product by HPLC assay is 100.00%. XRPD and DSC data of product is consistant with reference sample. MS (ES)=420 (M+1).

Example 5

Use of Morpholine as Both Reactant and Base in 2-Propanol as Solvent 7-(1-ethyl-propyl)-3-(2,4-dichloro-thiazol-5-yl)-2,5-dimethyl-pyrazolo[1,5-a]pyrimidine (11.64 mmoles) is charged into a 100 mL 3-necked round bottomed flask followed by addition of 2-propanol (16 mL, 3.72 volumes). The yellowish brown slurry is stirred at about 20° C. for 5 min. Then morpholine (3.3 g, 37.84 mmoles) is added over 2-5 minutes. Contents are refluxed for 6 hr. The slurry is cooled to 25° C. 2-Propanol (32 mL, 7.44 volumes) and water (8.6 mL, 2.0 volumes) are added and the mixture warmed to 70-75° C., filtered and concentrated to ~9 volumes at atmospheric pressure. The clear solution is gradually cooled to 55° C., seeded with 0.06 g of crystalline 7-(1-ethyl-propyl)-3-(4-chloro-2-morpholin-4-yl-thiazol-5-yl)-2,5-dimethyl-pyrazolo[1,5-a]pyrimidine slurried in 0.5 mL 2-propanol, rinsed with additional 0.5 mL 2-propanol and added to crystallization flask. The slurry is cooled to 0-5° C., maintained for 1 hr., filtered and the product rinsed with 2-propanol (9 mL, 2.1 volumes). Suctioned dried under vacuum at 60° C. to afford 4.6 g of dry 7-(1-ethyl-propyl)-3-(4-chloro-2-morpholin-4-yl-thiazol-5- yl)-2,5-dimethyl-pyrazolo[1,5-a]pyrimidine (88.8% yield, purity by HPLC assay is 99.88%). MS (ES)=420 (M+1).

Example 6

7-(1-ethyl-propyl)-3-(2,4-dichloro-thiazol-5-yl)-2,5-dimethyl-pyrazolo[1,5-a]pyrimidine 7-(1-ethyl-propyl)-3-iodo-2,5-dimethyl-pyrazolo[1,5-a]pyrimidine (10 g, 29.17 mmoles), 2,4-dichlorothiazole (5.2 g, 33.76 mmoles), cesium carbonate (19.9 g, 61.07 mmoles) and 1,10-phenanthroline (1 g, 5.5 mmoles) are charged into a 250 mL 3-necked round bottomed flask, followed by 2-MeTHF (36 mL, 3.6 volumes). The reaction mixture is degassed with nitrogen and then evacuated. Cuprous chloride (0.57 g, 5.7 mmoles), DMAC (10 mL, 1 volume) and 2-MeTHF (4 mL, 0.4 volumes) are added in succession. The reaction mixture is degassed with nitrogen and then evacuated. The contents are refluxed for 20 hr. The reaction mixture is cooled to ~70° C. and 2-MeTHF (100 mL, 10 volumes) is added. The contents are filtered at ~70° C. and the residual cake is washed with 2-MeTHF (80 mL, 8 volumes) at about 65-72° C. The filtrate is transferred into a separatory funnel and extracted with water. The organic layer is separated and washed with dilute HCl. The resulting organic layer is treated with Darco G60, filtered hot (60° C.). The filtrate is concentrated at atmospheric pressure to ~2.8 volumes. 25 mL 2-propanol is added, followed by re-concentration to ~2.8 volumes. An additional 25 mL 2-propanol is added, followed again by re-concentration to ~2.8 volumes. Finally, 48 mL 2-propanol is added. The contents are cooled to −7° C., maintained at −7° C. for 1 hr., filtered and rinsed with 20 mL chilled 2-propanol. Product is suction dried and then vacuum dried at 60° C. to afford 9.41 g 7-(1-ethyl-propyl)-3-(2,4-dichloro-thiazol-5-yl)-2,5-dimethyl-pyrazolo[1,5-a]pyrimidine (purity of product by HPLC assay is 95.88%). MS (ES)=369 (M+1).

Example 7

Synthesis of 7-(1-ethyl-propyl)-3-(2,4-dichloro-thiazol-5-yl)-2,5-dimethyl-pyrazolo[1,5-a]pyrimidine using 1,4-Dioxane solvent and CuCl catalyst

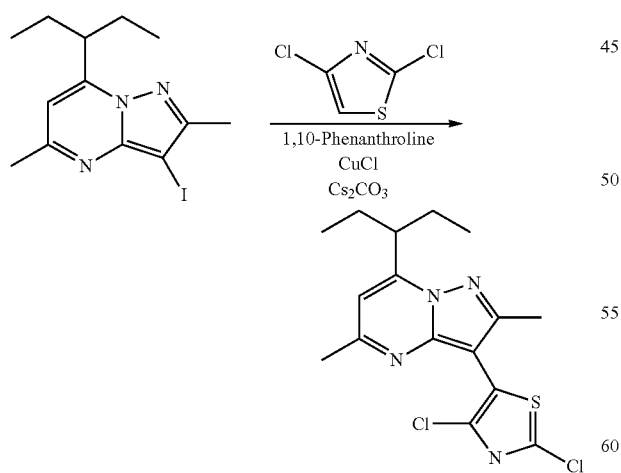

Add dioxane (9.06×), Cs$_2$CO$_3$ (2.00×), 7-(1-ethyl-propyl)-3-iodo-2,5-dimethyl-pyrazolo[1,5-a]pyrimidine (1.0 equivalent), 2,4-dichlorothiazole (0.54 equivalent) to a reactor under N$_2$. Purge the reactor with N$_2$ three times, degas with N$_2$ for 0.5~1 hr., and then add 1,10-phenanthroline (0.3 eq) and CuCl (0.3 eq) under N$_2$, degassing with N$_2$ for 0.5~1 hr. Heat the reactor to 100° C.~110° C. under N$_2$. Stir the mixture for 22~24 hr. at 100° C.~110° C. Cool to 10~20° C. and add water (10V) and CH$_3$OH (5V), stir the mixture for 1~1.5 hr. at 10~20° C. Filter the suspension, resuspend the wet cake in water, stirr for 1~1.5 hr. at 10~20° C., and filter the suspension again. Charge the wet cake to n-heptane (16V) and EtOAc (2V) under N$_2$. Heat the reactor to 40° C.~50° C. under N$_2$.

Active carbon (0.1×) is added at 40° C.~50° C. The reactor is heated to 55° C.~65° C. under N$_2$ and stirred at 55° C.~65° C. for 1~1.5 hr. The suspension is filtered at 40~55° C. through diatomite (0.4×). The cake is washed with n-heptane (2.5V). The filtrate is transferred to another reactor. EtOAc (10V) is added and the organic layer washed with 2 N HCl (10V) three times, followed by washing two times with water (10×, 10V). The organic layer is concentrated to 3~4V below 50° C. The mixture is heated to 80~90° C. The mixture is stirred at this temperature for 40~60 min. The mixture is cooled to 0~5° C., stirred for 1~1.5 hr. at 0~5° C. and filtered. The cake is washed with n-heptane (1V) and vacuum dried at 45~50° C. for 8~10 hr. The crude product is dissolved in 2-propanol (7.5V) under N$_2$, and re-crystallized with 2-propanol. The cake is dried in a vacuum oven at 45° C.~50° C. for 10-12 hr. (55~80% yield). $^1$H NMRδ6.537 (s, 1H) 3.591-3.659 (m, 1H, J=6.8 Hz), 2.593 (s, 3H), 2.512 (s, 3H), 1.793-1.921 (m, 4H), 0.885-0.903 (m, 6H).

We claim:

1. A compound of the formula

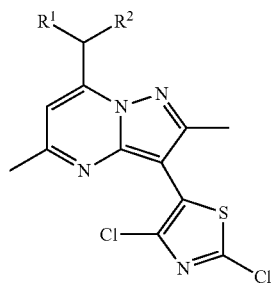

wherein:
R$^1$ and R$^2$ are independently ethyl or n-propyl;
or a salt thereof.

2. The compound according to claim 1, or a salt thereof, wherein R$^1$ and R$^2$ are each ethyl.

3. A synthetic process for preparing a compound of the formula

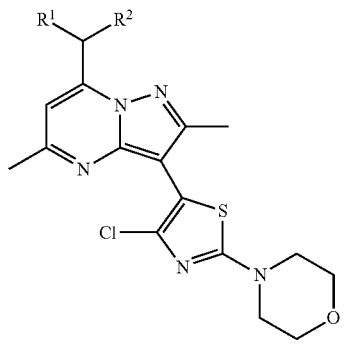

wherein R¹ and R² are independently ethyl or n-propyl, comprising the steps of i) reacting a compound of the formula

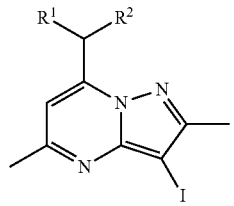

or a salt thereof, with 2,4-di-chlorothiazole, or a salt thereof, in the presence of a copper halide catalyst, a ligand selected from 1,10-phenanthroline and bipyridine, and a base selected from $K_3PO_4$ and $Cs_2CO_3$, in the presence of a suitable solvent, to form a compound of the formula

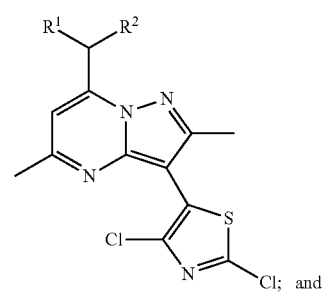

ii) reacting the product of step i), with morpholine, or a salt thereof, in the presence of a suitable inorganic base and solvent.

4. The process according to claim 3 wherein R¹ and R² are each ethyl.

5. The process according to claim 3 wherein the copper halide is CuCl.

6. The process according to claim 3 wherein the ligand is 1,10-phenanthroline.

7. The process according to claim 3 wherein the base in step i) is $Cs_2CO_3$.

8. The process according to claim 3 wherein the base in step ii) is $K_2CO_3$.

9. The process according to claim 3 wherein R¹ and R² are each ethyl, the copper halide is CuCl, the ligand is 1,10-phenanthroline, the base in step i) is $Cs_2CO_3$, and the base in step ii) is $K_2CO_3$.

10. The process according to claim 9 wherein the solvent for step i) is 1,4-Dioxane or 2-MeTHF/DMAC and the solvent for step ii) is morpholine, 2-MeTHF, or 2-propanol.

11. A synthetic process for preparing a compound of the formula

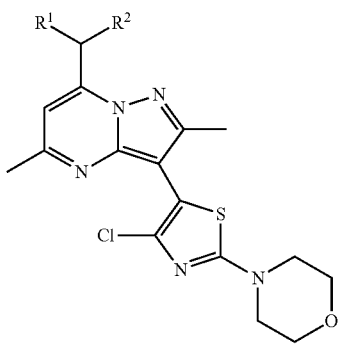

wherein R¹ and R² are independently ethyl or n-propyl, comprising the steps of i) reacting a compound of the formula

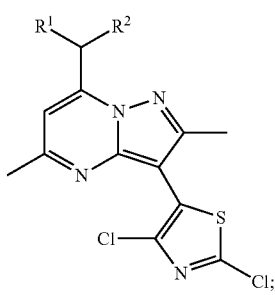

or a salt thereof, with excess morpholine or salt thereof, in the presence of a suitable solvent.

12. The process of claim 11 wherein the solvent is 2-methyl tetrahydrofuran.

13. The process of claim 11 wherein the solvent is 2-propanol.

14. The process of claim 11 wherein R¹ and R² are each ethyl.

15. A synthetic process for preparing a compound of the formula

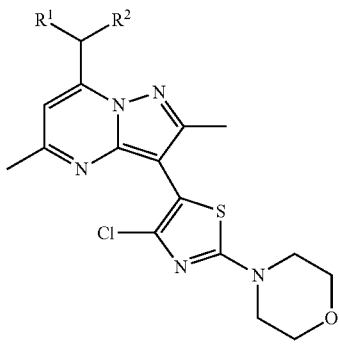

wherein R¹ and R² are independently ethyl or n-propyl, comprising the steps of i) reacting a compound of the formula

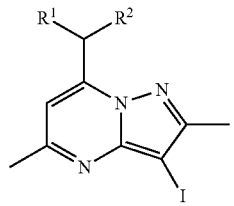

or a salt thereof, with 2,4-di-chlorothiazole, or a salt thereof, in the presence of a copper halide catalyst, a ligand selected from 1,10-phenanthroline and bipyridine, and a base selected from $K_3PO_4$ and $Cs_2CO_3$, to form a compound of the formula

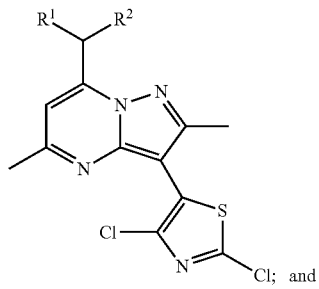

ii) reacting the product of step i), with an excess of morpholine, or a salt thereof, in a suitable solvent.

16. The process of claim 15 wherein the solvent is 2-methyl tetrahydrofuran.

17. The process of claim 15 wherein the solvent is 2-propanol.

18. The process of claim 15 wherein R¹ and R² are each ethyl.

* * * * *